(12) United States Patent
Stapf et al.

(10) Patent No.: US 7,041,123 B2
(45) Date of Patent: May 9, 2006

(54) WARMING PACK WITH TEMPERATURE UNIFORMITY AND TEMPERATURE STABILIZATION

(75) Inventors: Donald Stapf, Minneapolis, MN (US); Keith J. Leland, Plymouth, MN (US)

(73) Assignee: Arizant Technologies LLC

( * ) Notice: Subject to any disclaimer, the term of this patent is extended or adjusted under 35 U.S.C. 154(b) by 312 days.

(21) Appl. No.: 10/205,157

(22) Filed: Jul. 25, 2002

(65) Prior Publication Data

US 2003/0097164 A1    May 22, 2003

Related U.S. Application Data

(60) Provisional application No. 60/311,756, filed on Aug. 9, 2001.

(51) Int. Cl.
*A61F 7/00* (2006.01)

(52) U.S. Cl. .............................. 607/108; 607/114; 62/4

(58) Field of Classification Search ................ 607/114, 607/108–112; 604/113, 291, 292, 293; 602/19, 602/27, 41; 126/263, 204, 206, 263.01; 428/402; 62/4, 457, 112, 53, 530; 44/250–253; 206/484, 206/484.1, 484.2; 36/2.6; 383/100–102, 383/109
See application file for complete search history.

(56) References Cited

U.S. PATENT DOCUMENTS

| | | | | |
|---|---|---|---|---|
| 4,427,010 A | * | 1/1984 | Marx | ........................ 607/114 |
| 4,522,190 A | * | 6/1985 | Kuhn et al. | ............. 126/263.02 |
| 4,756,299 A | * | 7/1988 | Podella | ................... 126/263.02 |
| 5,010,883 A | | 4/1991 | Rawlings et al. | |
| 5,018,515 A | | 5/1991 | Gilman | |
| 6,099,556 A | * | 8/2000 | Usui | .......................... 607/114 |
| 6,158,427 A | * | 12/2000 | McGuire et al. | ........ 126/263.01 |
| 6,319,599 B1 | * | 11/2001 | Buckley | .................. 428/308.4 |
| 6,393,843 B1 | * | 5/2002 | Kohout | ............................. 62/4 |
| 2002/0045923 A1 | | 4/2002 | Tone et al. | |

OTHER PUBLICATIONS

Himran, S. et al., "Characterization of Alkanes and Paraffin Waxes for Application as Phase Change Energy Storage Medium," Energy Sources, vol. 14, p. 117-128.
Sparrow, E.M., et al., "Correlation of Melting Results for Both Pure Substances and Impure Substances," Journal of Heat Transfer, Aug. 1986, vol. 108, p. 649-653.
Author Unknown, Minifibers, Inc., "Fiber Properties, Short Stuff® Synthetic Fiber," 1 pg.
Author Unknown, Minifibers, Inc., "Short Stuff® Polyethylene Physical & Chemical Characteristics," 1 pg.

* cited by examiner

*Primary Examiner*—Rosiland Rollins
(74) *Attorney, Agent, or Firm*—Incaplaw; Terrance A. Meador

(57) ABSTRACT

A warming pack includes a container in the form of a pack, pouch, or bag in which reactants for an exothermic chemical reaction are distributed in one or more flexible matrixes that prevent them from shifting. The rate of the reaction is controlled and the reaction is thermally buffered in order that heat be produced at a constant rate.

32 Claims, 5 Drawing Sheets

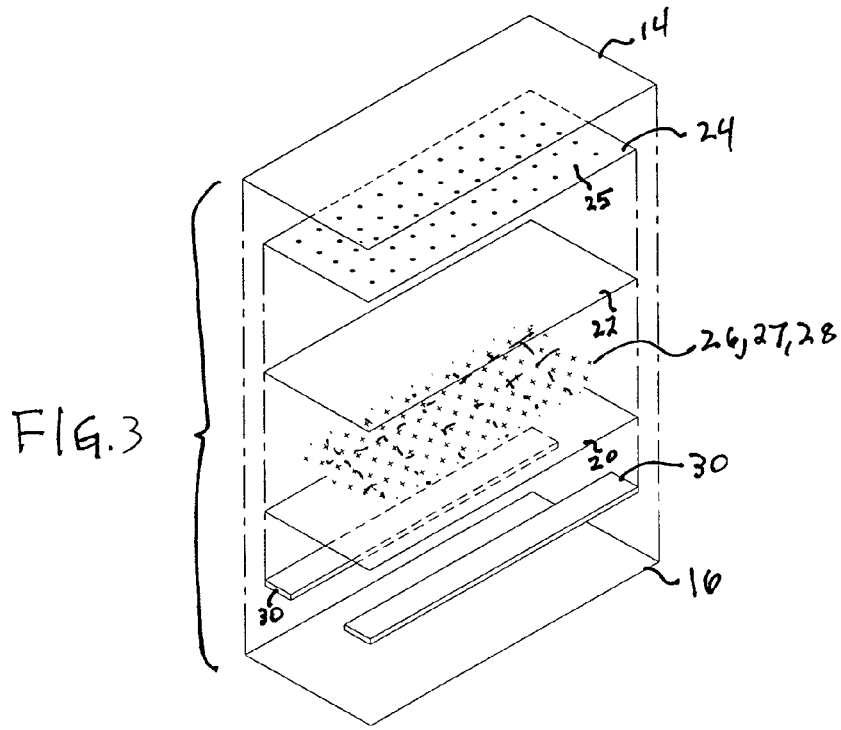
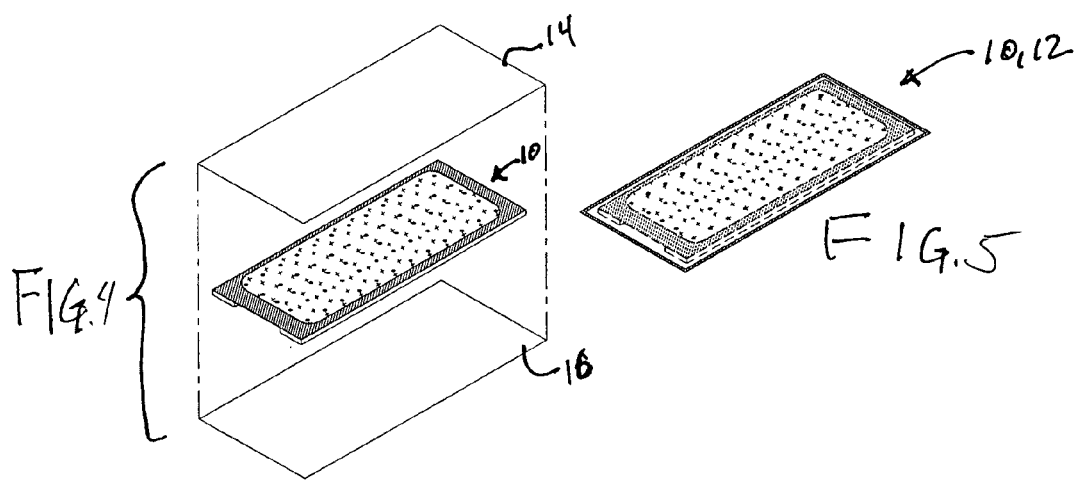

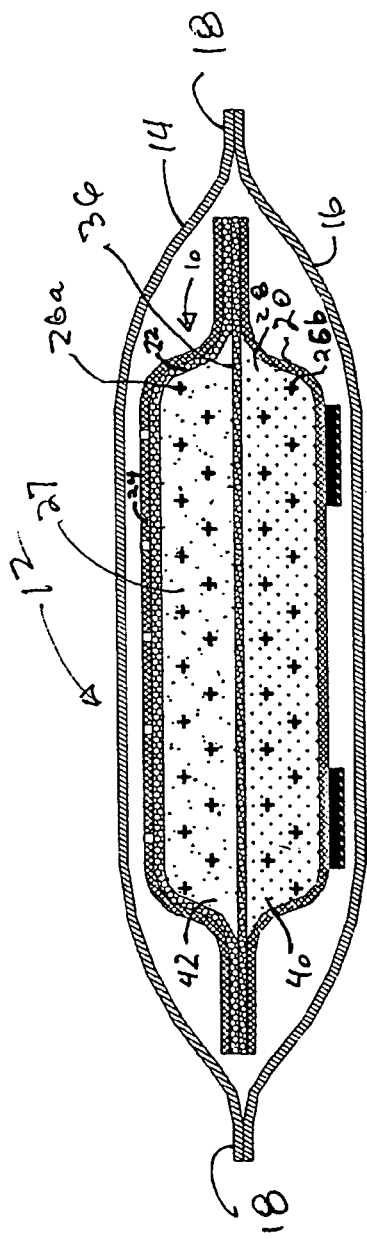
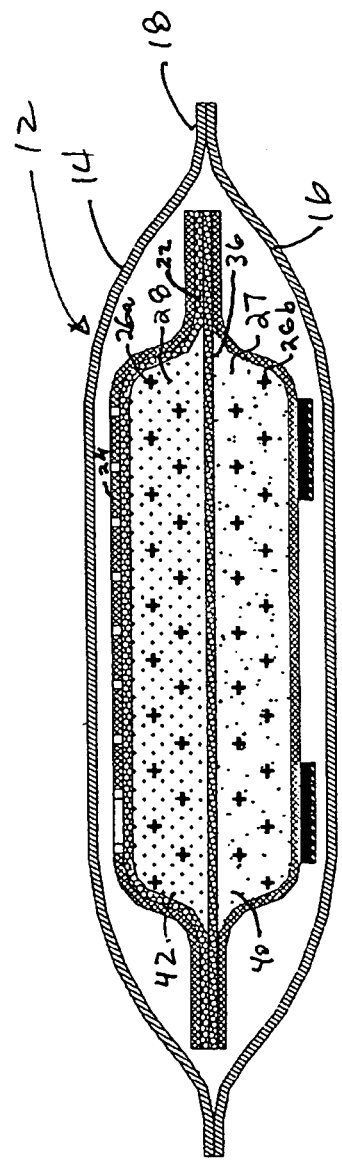

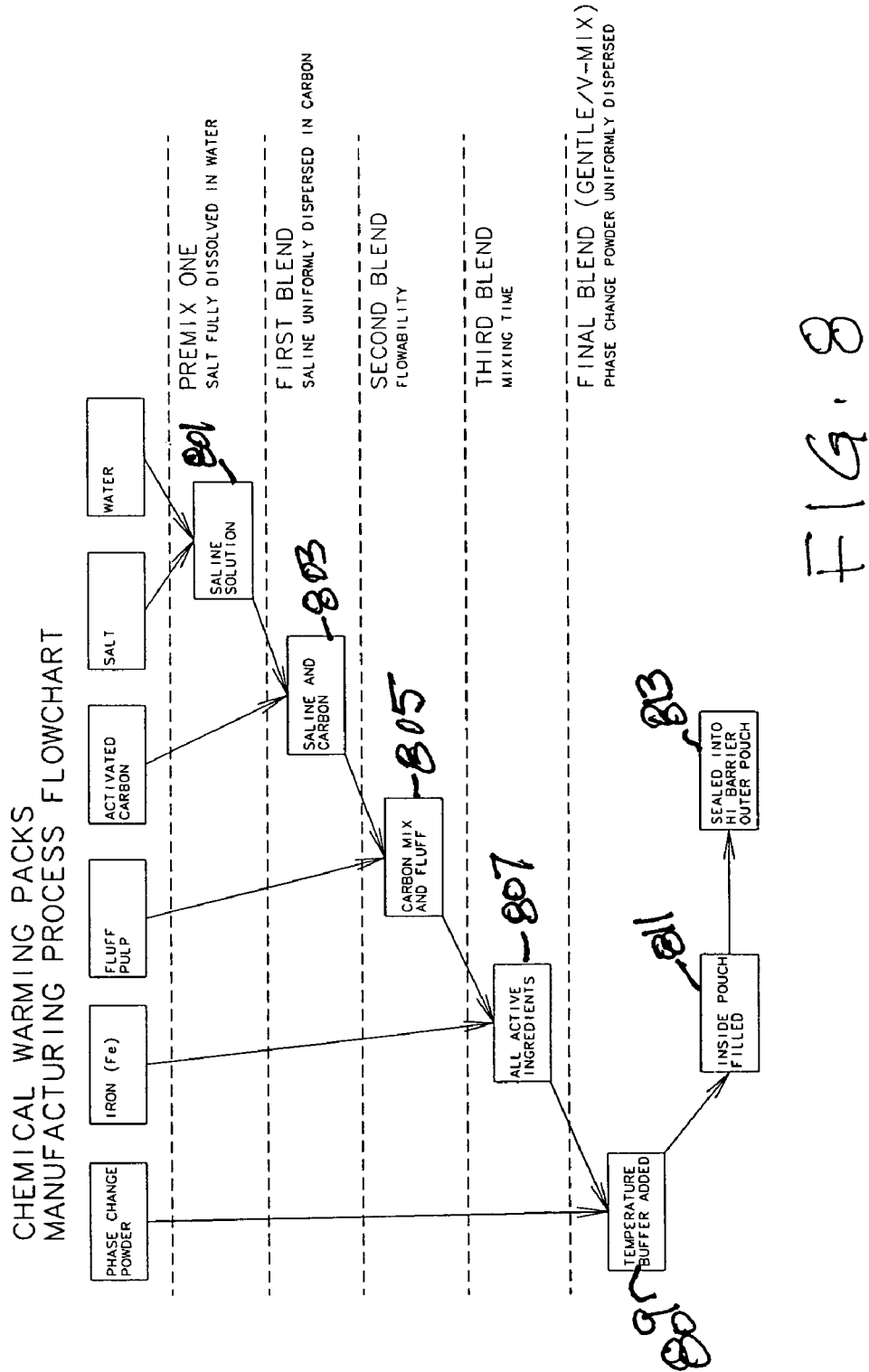

WARMING PACK WITH TEMPERATURE UNIFORMITY AND TEMPERATURE STABILIZATION

Priority is claimed to U.S. Provisional Patent Application No. 60/311,756, filed on Aug. 9, 2001 for "Warming Pack With Temperature Uniformity and Temperature Stabilization".

BACKGROUND OF THE INVENTION

This invention relates to devices that generate heat by non-electrical means for the purpose of warming. In particular, the invention relates to a warming pack which generates heat that is used for warming objects such as tissue. In such a device, heat may be generated by an exothermic chemical reaction that takes place within the warming pack. Warming packs that operate based on exothermic chemical reactions are capable of storing energy at ambient temperatures for extended periods of time and then being brought into use very quickly.

A significant problem attending the use of a warming pack is spatial non-uniformity of temperature produced by the warming pack. The material comprising the reactants that drive the heat-generating chemical reaction tends to move or shift during handling of the device. The material is usually in a particulate, powdered or granular form, making it more difficult to contain as the size of a warming pack increases. As the material shifts, localized concentrations can occur within a warming pack, producing variations in temperature across a surface of a warming pack through which heat is transferred for warming. Such concentrations can produce hot and cold spots in a warming pack during operation.

A second problem with warming pack operation is temporal non-uniformity of temperature produced by the warming pack. Chemical warming packs are designed to operate within a temperature range that is safe and effective for some intended use. However, such devices utilize a constant heat generation process, not a constant temperature process. For example, chemical warmers that generate heat via the reduction-oxidation of iron with oxygen can achieve a constant rate of heat generation by metering the amount of oxygen available to react with the iron. For such a pack the quantity of heat that can be generated depends on the amount of iron available. The duration of heat generation depends on the amount of iron available and the rate at which oxygen is made available to react with the iron. Both of these factors are predetermined by the design of the pack. The final steady state operating temperature, however, depends on the heat generation rate and ambient conditions, including temperature. The operating temperature of such chemical warming packs, therefore, will vary with the deviation of ambient conditions from those assumed in the design of the pack.

SUMMARY OF THE INVENTION

The invention solves the problems of temperature non-uniformity caused by shifting of the material within a warming pack and temperature variation produced by operation of the warming pack in varying and variable ambient conditions.

Temperature non-uniformity is reduced by maintaining a uniform distribution of the material comprising the reactants within the warming pack. This is realized, for example, by disposing the reactant material in a matrix of inactive material. Temperature variability is reduced by controlling the heat-generating reaction. This may be accomplished by modulating the rate of the reaction. It can also be accomplished by buffering heat produced by the reaction as it proceeds.

The achievement of these objectives by the invention can be understood by the following detailed description, examples, and the drawings described below.

BRIEF DESCRIPTION OF THE DRAWINGS

FIG. 3 is an exploded perspective view of the warming pack of FIGS. 1 and 2.

FIG. 4 is a perspective partially assembled view of the warming pack of FIGS. 1 and 2.

FIG. 5 is a perspective view of the warming pack of FIG. 1.

FIG. 6 is a side sectional view of another embodiment of the invention.

FIG. 7 is a side sectional view of yet another embodiment of the invention.

FIG. 8 is a flow diagram of an exemplary procedure for making a warming pack according to the invention.

DETAILED DESCRIPTION OF THE PREFERRED EMBODIMENTS

Figure 1:
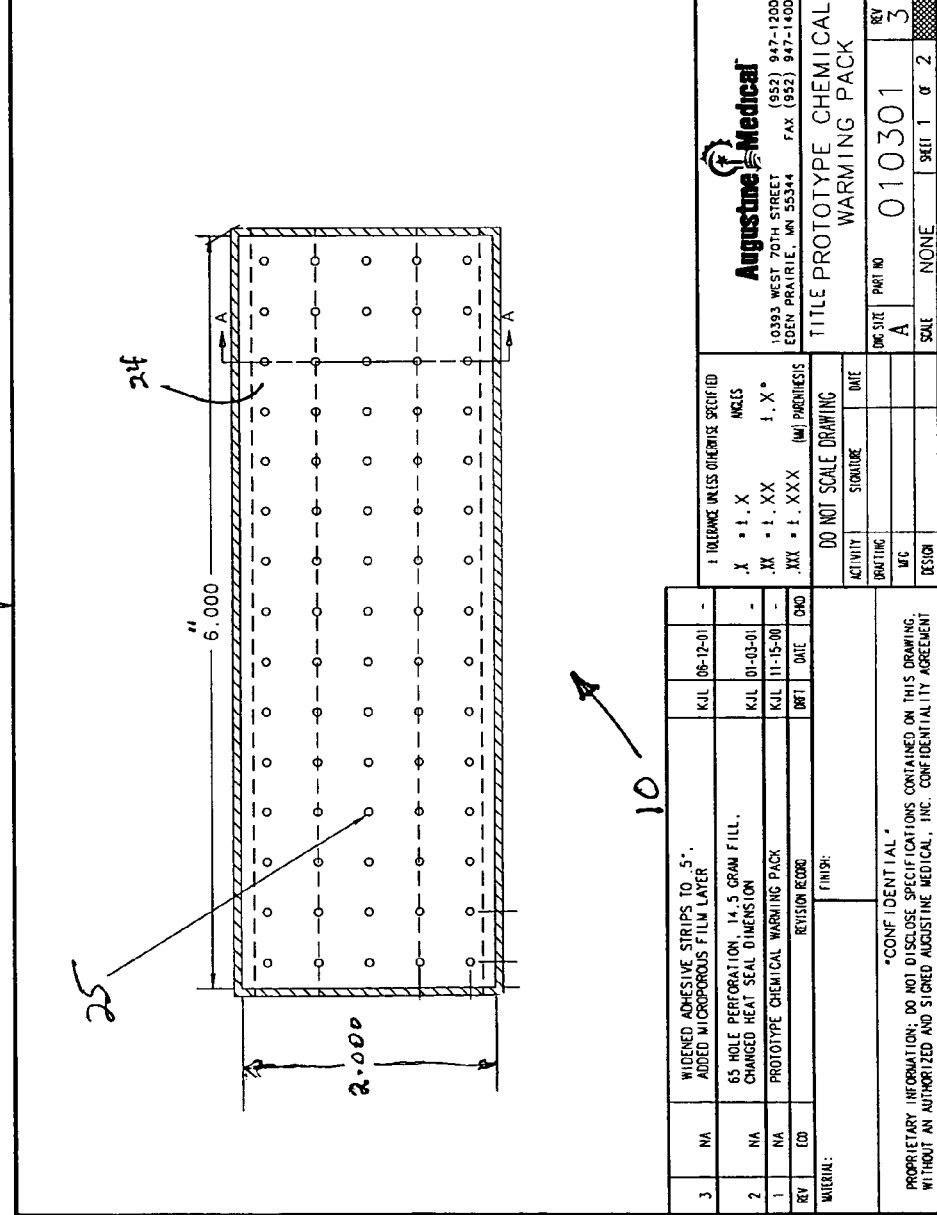
FIG. 1 is a top plan view of a warming pack according to a first embodiment of this invention.
Figure 2:
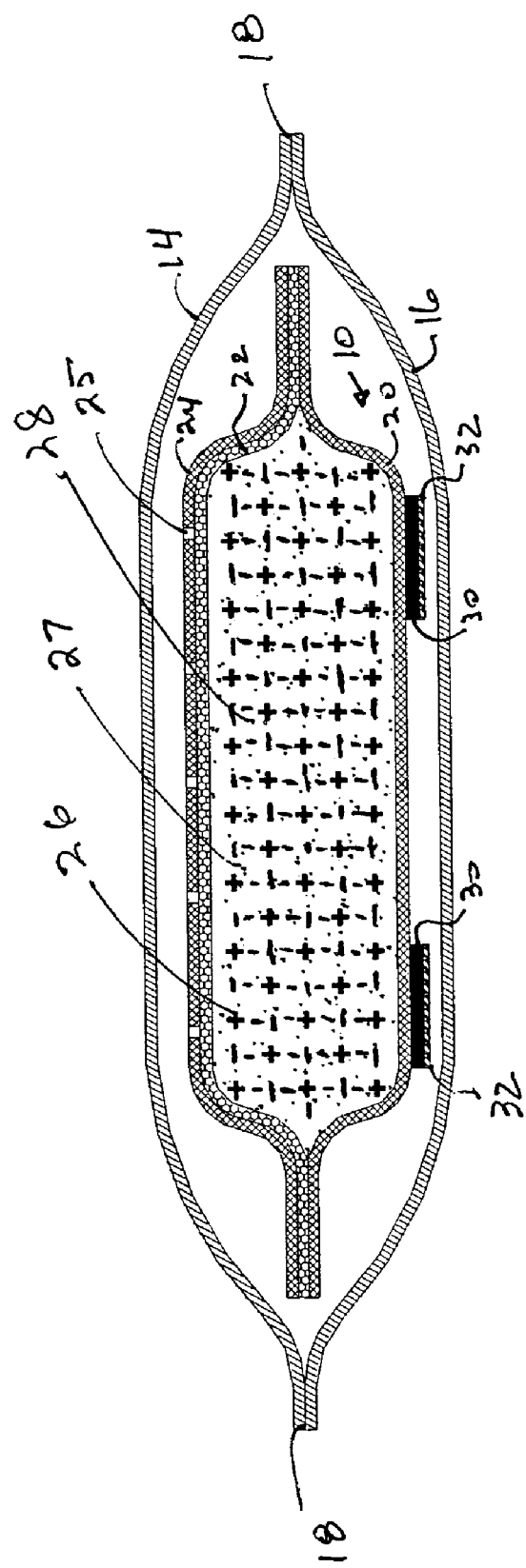
FIG. 2 is a sectional view taken along the line A—A of FIG. 1.

The invention is referred to as a "warming pack." In this regard, the invention may be also referred to as a warming pouch, a warming bag, a warming pad, and other equivalent terms. The warming pack operates by means of an exothermic reaction that takes place within the warming pack. The reaction is chemical and is caused or driven by reactant material within the warming pack.

Refer to FIGS. 1–5 for an understanding of the invention. The invention is a warming pack 10. A matrix of flexible, compressible material is disposed in the warming pack; this element is hereinafter referred to as a "matrix," and is indicated in the drawings by reference numeral 26. The term "matrix" is used in its broad sense to indicate a three-dimensional material structure in which reactant material 27 is loosely contained, suspended, bound, or embedded. The reactant material, typically a mixture of materials in a particulate, powdered or a granulated form, is distributed, substantially uniformly throughout the matrix 26. The matrix 26 is densely packed within the warming pack 10, thereby preventing it from shifting within the warming pack 10. The warming pack 10 is a flexible package having a first flexible sheet 20 composed of a material that is vapor impermeable. A second flexible sheet 22 of the warming pack 10 is composed of a material that is impermeable to particulate matter but which is vapor-permeable. As used herein, the term vapor is meant to be inclusive of all gases whether or not their natural state is a liquid, gas or solid. The sheet 22 keeps the relatively large particles of the reactant material 27 confined within the warming pack 10, but permits the relatively smaller molecules of oxygen into the interior of the warming pack where they react with the material 27. The first and second sheets 20 and 22 are joined around their peripheries by thermal bonding, ultrasonic bonding, gluing or any other equivalent procedure suitable for joining the sheets with a particulate-impermeable seal. The reactant material 27 is relatively uniformly distributed throughout the matrix 26, thereby reducing or preventing shifting of the material during handling and use of the warming pack 10.

Suitable materials for the elements thus far described are known and available. The first flexible sheet 20, for example, may be a structure constituted of one or more flexible plastic materials and made to be gas-impermeable; such materials may be embodied in non-woven, laminated plastic sheets of polyethylene, polypropylene, and other equivalents. The second flexible sheet 22 may be a structure constituted of one or more flexible plastic materials such as sheets of microporous polyethylene, polypropylene, or other equivalents. The matrix 26 may be a flexible, compressible structure constituted of a fibrillated batting material consisting of fibers of polyethylene, polyester, cellulose, or other equivalents. The reactant material 27 is a mixture of ingredients that, upon exposure to oxygen, undergoes an exothermic reaction. Such mixtures are known and may include, for example, iron, carbon, salt, and water.

As thus described, the warming pack 10 operates as follows: The reactant material 27, contained in the matrix 26, undergoes an exothermic reaction when exposed to oxygen. Oxygen enters the warming pack 10 through the microporous, vapor-permeable sheet 22. As the reaction proceeds, heat is generated. An amount of the heat generated is transferred, by radiation, convection and conduction, through the particulate and vapor-impermeable sheet 20. It is this sheet that is intended to act against an object to be heated. The outside surface of the first sheet 20 may be brought into direct contact with the object, or it may act through or by way of some structure, or element between it and the object. The substantially uniform distribution of the reactant material 27 within the matrix 26 contained in the warming pack 10 results in substantially uniform distribution of heat across and through the first sheet 20.

Control of the reaction which produces heat is also contemplated in this invention in order to maintain a substantially constant (or very slowly changing) temperature for the duration of the reaction. In the invention this may be accomplished by modulating the rate of the reaction, by buffering heat produced by the reaction as it proceeds, by both techniques, and by other equivalent techniques. In this regard, the reaction rate is modulated by provision of a third flexible sheet 24 having a fixed, predetermined, or otherwise selectable permeability to air. The sheet 24 is placed on and attached to the vapor-permeable sheet 22. Oxygen that passes through these two sheets drives the exothermic reaction. The rate at which oxygen passes through these sheets is governed by the permeability of the third sheet 24. In the embodiments of the invention, the permeability of the sheet 24 to air is fixed by selection of a sheet material that is vapor-impermeable and provision of apertures 25 that are made in the sheet 24. Such apertures, or equivalent structures permit oxygen to approach the reactant material 27 at a determinable rate. The rate of air passing through the sheets 24 and 22 dampens, controls or modulates the rate at which the exothermic reaction progresses, thereby causing it to reduce the rate at which the operating temperature produced by the reaction changes. The third flexible sheet 24 may be a structure constituted of one or more flexible plastic materials that are impermeable to water and oxygen; such materials may include sheets of polyethylene, polypropylene, and other equivalents; so constituted, the third sheet 24 would be perforated with small apertures to yield a known permeability to air.

Heat produced by the reaction may also be buffered by the provision of a temperature sink in the form of a material brought into thermal association with the reactant material 27. In this regard, a thermal buffer material 28, also in particulate form, is distributed substantially uniformly throughout the matrix 26 in thermal association with the reactant material 27. In fact, it is preferred, although not required, that the reactant material 27 and the buffer material 28, be mixed prior to being received in the matrix 26. The exothermic reaction is buffered by the material 28. Preferably the buffer material 28 is constituted of a phase change material (PCM) that helps limit the maximum temperature achievable by the on-going reaction. Such materials are available as a fine powder of free flowing particles.

Thus, the structure and materials of the warming pack 10 solve the two problems set forth above. That is, the matrix 26 maintains the spatial uniformity of the temperature throughout the warming pack 10 by preventing or substantially reducing the ability of the reaction material 26 to shift, while controlled permeability and provision of the buffer limit and smooth out the temporal variation in temperature as the exothermic reaction progresses within the warming pack 10.

In order to permit the warming pack 10 to be handled for shipment, storage, and distribution for use, it is initially disposed in a container that is impermeable to particulate matter and to vapor. For example, such a container may be realized by an impermeable bag 12 formed by bringing two sheets 14, 16 together with the warming pack 10 therebetween and sealing them around their peripheries by a vapor impermeable seal 18. The sheets 14, 16 are formed of one or more materials that are impermeable to particulate material and to air. Such materials may include sheets of high oxygen barrier laminate films incorporating SARAN™ or metallized foils or films, or other equivalents. The bag 12 provides a clean, oxygen free environment for containment of the warming pack until it is ready for use. When use is desired, the bag 12 is breached by cutting or tearing either or both of the sheets 14, 16 and removing the warming pack 10. Air containing oxygen immediately passes into the warming pack 10 through the third and second sheets 24, 22. The oxygen initiates and maintains an exothermic chemical reaction with the reactant material 27. As the reaction progresses, heat that is generated flows throughout the materials inside the warming pack 10. Some of the heat passes through the first sheet 20 whence it is applied to an object to be warmed.

An additional element may be employed for convenience. That is, lightly tacky adhesive strips 30 with release liners 32 may be disposed on the outer surface of the first sheet 20 to assist in attaching the warming pack 10 for use. Other, equivalent materials and structures may be used as substitutes for, or to augment, the strips 30.

A second embodiment of the invention is illustrated in FIG. 6. In FIG. 6, the warming pack 10 has a fourth flexible sheet 36 disposed between the first and second sheets 20 and 22 and sealed at its periphery to the peripheries of those two sheets by the impermeable seal 18. The fourth sheet 36 bifurcates the space within the warming pack 10, forming a first chamber or space 40 and a second chamber or space 42. In the orientation shown, the first chamber or space 40 is disposed below the second chamber or space 42. The fourth flexible sheet 36 may be made of the same material as the first sheet 20. In this embodiment, a first matrix 26a is disposed, slightly compressed, in the second chamber or space 42, that is, between the fourth sheet 36 and the second sheet 22, with the reactant material 27 disposed substantially uniformly in it. A second matrix 26b is disposed, slightly compressed, in the first space 40, that is, between the fourth sheet 36 and the first sheet 20, with the buffer material disposed substantially in it. In this embodiment, when the warming pack 10 is removed from the container 12 and deployed for use, the buffer material 28 is disposed against, although separate from the reactant material 27.

A third embodiment of the warming is illustrated in FIG. 7. The structure of the warming pack 10 in this embodiment is identical with that of the second embodiment. However, the locations of the reactant and buffer materials 27 and 28 are reversed. That is, the matrix 26b is disposed, densely packed, in the first chamber or space 40, between the fourth sheet 36 and the first sheet 20, with the reactant material 27 disposed substantially uniformly in it. The matrix 26a is disposed in the second chamber or space 42, between the fourth sheet 36 and the second sheet 22, with the buffer material 28 disposed substantially uniformly in it. In this embodiment, the fourth sheet 36 is made of gas-permeable material. Oxygen approaches the reactant material 27 through the permeability-controlled structure comprising the sheets 22, 24, the buffer material 28, and the vapor-permeable sheet 36.

EXAMPLE 1

The following description sets forth the materials and steps utilized in making one example of a warming pack according to this invention. In this example, the warming pack operates by using the thermal energy released by the reduction/oxidation reaction of iron with oxygen in the presence of a buffer material embodied as a phase change powder to prevent the warming pack from attaining temperatures above 42° C. Both the reactant material (iron, carbon, salt, and water) and the buffer material (hydrophobic RT 40 powder, a paraffin) are disposed in a matrix of fluff pulp material.

Ingredients:
  Active Ingredients: (per warming pack)
    Reduced, Extra Fine Iron Powder (325 mesh)—2 grams
    Powdered Activated Carbon Premix—3 grams
    Premix ratios: 15 grams activated carbon, 2 grams sodium chloride, 20 milliliters water
  Inactive ingredients:
    Hydrophobic RT 40 powder—10 grams
    Polyethylene fluff pulp, classified fiber length 0.55–0.8 mm, or 1.0 mm—1 gram
  Primary Warming Pack Material:
    0.9–2.0 ounce polypropylene nonwoven laminated to 0.75–1 mil polypropylene film
    3M Propore microporous polypropylene film
    Avery Dennison FT 8306 Permanent/removable PSA combination w/release liner
  Secondary Packaging Material:
    50 gauge SARAN™ coated PET/LLDPE high barrier laminate film Manufacturing Method Refer to FIGS. 1–5 and 8. Warming packs according to the first embodiment are created by thermally welding layers of perforated olefin film/nonwoven laminate (third flexible sheet 24), gas-permeable film (second flexible sheet 22), and non-perforated olefin film/nonwoven laminate (first flexible sheet 20), with the resultant warming pack 10 having the gas-permeable layer (second flexible sheet 22) in the middle and the nonwoven layers (third and first flexible sheets 24, 20) facing outwards. Adhesive strips 30 are applied to the external surface of the non-perforated nonwoven laminate constituting the first flexible sheet 20.

The warming pack has a dimensional footprint shown in FIG. 1. The footprint (in plan) is rectangular, dimensioned at 5.08 cm (2") width (W) by 15.24 cm (6") length (L). The third flexible sheet 24 has a regular two dimensional array of apertures formed in it (prior to thermal welding of the sheets 20, 22, 24). The apertures are formed by 0.05461 cm (0.0215") diameter pins at a density of 0.97 apertures per square centimeter (6.25 apertures per square inch).

As shown in FIG. 8, the ingredients set forth above are combined in the proportions set forth in the following table, and then warming packs are filled to yield the warming device of this invention. In this regard, first reactant constituents (salt, water, and carbon) are prepared. In step 801, water and salt are mixed to form a saline solution in which the salt is fully dissolved in the water. In step 803, the saline solution is mixed with the carbon powder to form a mixture in which the saline solution is substantially uniformly distributed in the carbon. The carbon powder absorbs the saline solution to form unevenly sized particles, and the saline/carbon mixture is blended to make the particle size substantially uniform. In step 805, the carbon/saline mixture is then blended with the fluff pulp matrix material such that the carbon mixture disperses and coats the polyethylene fibers of which the matrix 26 is constituted. This yields a first mixture. In step 807, the iron powder is added to the first mixture to yield a second mixture. The second mixture ingredients are blended to adequately disperse the fine iron particles. In step 809, the hydrophobic RT40 powder is (the thermal buffer material) added to the second mixture using a final blending procedure (V-blend for example). This yields a third mixture. In step 811, a pack filling operation is performed where a known amount of the third mixture (16 grams per 2"×6" pack) is introduced into a warming pack 10, which is then sealed. In step 813, the warming pack 10 is sealed into the impermeable bag 12.

Recipe per 2"×6" Warming Pack

| Component | Quantity | Unit of Measure |
| --- | --- | --- |
| Iron (Fe) | 2.0 | Grams |
| Carbon (C) | 1.22 | Grams |
| Sodium Chloride (NaCl) | 0.16 | Grams |
| Water | 1.62 | Milliliters |
| Fluff Pulp | 1.0 | Grams |
| Phase Change Material (PCM) | 10.0 | Grams |

In this manufacturing method, steps 803–809 include blending operations that are performed under conditions that achieve substantially uniform mixtures, without substantially altering the constituents of each mixture. For example, in steps 805, 807, and 809 the blending action should not reduce the average fiber length in order that the structural characteristics of the matrix not be weakened. That is, the fiber is specified at a certain classified fiber length (mean length per fiber) which is selected to keep the matrix from shifting during manufacturing, shipment, storage, and preparation for use of a warming pack. Blending should not change this value. In step 809, blending intensity must be limited to a level that will not separate the previously-blended constituents while the thermal buffer material is being added and mixed into the third mixture. Consequently, low shear blending, ribbon blending, or V-blending are preferred for the mixing steps. Further, steps 807, 809, 811, and 813 are performed in oxygen-free atmospheres or environments in order to suppress the exothermic reaction.

Raw Material Suppliers

Iron Powder (Mallinckrodt, Inc. 325 Mesh Iron Reduced Extra Fine Powder Food Grade. Code: 4348)

Chem/Serv
715 S.E. 8th Str.
Minneapolis, Minn. 55414
(612) 379-4411
(612) 379-8244 (Fax)
Activated Carbon Powder (Darco G-60/KB-B/S-51FF-TBD)
Van Waters and Rogers, Inc.
845 Terrace Court
St. Paul, Minn. 55101
651-774-9400
651-774-0850 (Fax)
Sodium Chloride (NaCl)
Sigma Aldrich
3050 Spruce Str.
Phase Change Powder—Hydrophobic RT40 Powder (60% RT40/40% Hi-Sil H303 Hydrophobic Silica)
Phase Change Laboratories
7920 Airway Rd.
Suite A-10
San Diego, Calif. 92154
(619) 671-9077
Polyethylene Fluff Pulp—Short Stuff® synthetic fiber
Minifibers, Inc.
2923 Boones Creek Road
Johnson City, Tenn. 37615
(423) 282-4242
3M—Propore™ Microporous Film
Avery Dennison—FT 8306 Pressure Sensitive Adhesive The table below sets forth five examples of reactant and buffer material mixtures that the inventors have tested in the warming pack configuration illustrated in FIGS. 1–5 and used in example 1. Notes following the table contain observations respecting the performances of the exemplary warming packs.

Five Examples

| Example | Iron (g) | Carbon (g) | Salt (g) | Fiber (g) | Phase Change Material (g) |
|---|---|---|---|---|---|
| 1 | 2.5 | 1.2 | .16 | .5 | 10 |
| 2 | 2.5 | 1.2 | .16 | .5 | 10 (85/15 hydrophilic silica) |
| 3 | 2 | 1.2 | .16 | .5 | 9 |
| 4 | 2.5 | 1.2 | .16 | .5 | 15 |
| 5 | 2.5 | 1.2 | .16 | .5 | 5 |

All examples are specific for a 2"×6" warming pack with 75 perforations formed by pins 0.021" in diameter. All phase change material consists of a paraffin mixed 60%/40% by weight with hydrophobic silica unless otherwise noted.

EXAMPLE 1

This example is for a stock 2"×6" warming pack capable of operating at temperatures between 35 and 43° C. for 60 to 180 minutes.

EXAMPLE 2

This example differs from example 1 in the composition of the phase change material. A higher percentage by weight of paraffin is incorporated resulting in greater energy storage capabilities but reduced resistance to material leaching. The drawback to this case is that any exposure to temperatures above the melting point of the phase change material will render the warming pack inert prior to actual activation by exposure to oxygen.

EXAMPLE 3

This reactant mix of this example has a slightly lower quantity of iron, resulting in shorter burn time and lower achieved temperatures.

EXAMPLE 4

This example has a larger quantity of phase change material which enables it to buffer a greater amount of energy when use conditions prevent heat loss to the ambient. Examples would include extremely warm ambient temperatures, warm target temperatures, or large amounts of backing insulation such as blankets.

EXAMPLE 5

This example has a lesser quantity of phase change material that reduces the bulk and cost of the warming pack, but also reduces the ability of the pack to buffer temperature. Possible applications include usage in relatively well controlled conditions, such as inpatient applications or under the supervision of a skilled caregiver.

These recipes worked well for the ingredients used. Altering the reactivity, particle size, mixing methods, air permeability of the packaging, fiber length, and other characteristics will also result in performance changes which may or may not be desirable. The particular recipe chosen will be determined by the characteristics of the ingredients used, manufacturing requirements and intended use. Alternative equivalent materials may be used without departing from the scope and spirit of the invention. Such materials could require changing the ratios of the ingredients, but would not change their function.

The shape (rectangular) and dimensions (2" by 6") of the warming pack are effective for the preferred embodiment, although they are not intended to limit the scope of the invention. The spatial uniformity of the temperature produced by the warming pack is enhanced by the rectangular shape, which reduces the effects that the edges of the warming pack have on the conduction of temperature laterally in the device. The size of the warming pack is well suited to the structural integrity of the matrix of fibrillated material; larger dimensions will tend to produce movement of the matrix material when the warming pack is held on one of its edges, for example. Nevertheless, those skilled in the art will appreciate that this invention can be practiced with other combinations of shape, size, and materials as may be appropriate for any particular design.

Geometry (Material Shifting and Temperature Uniformity Effects)

The preferred geometry of the warming pack impacts the propensity of the filler material to shift and the uniformity of the achieved surface temperature.

The preferred geometry of the current warming pack can be described as thin, narrow, and long (0.25"×2"×6"). Material shifting is most likely to occur when the long dimension of the warming pack is in the vertical orientation. Very little shifting is possible when the 2" or 0.25" dimension is oriented vertically. Furthermore, the 2"×0.25" dimensions create a cross section that reduces shifting even when the 6" dimension of the warming pack is oriented vertically. The 0.25" thickness is determined by the volume of ingredients necessary to achieve the desired warming characteristics.

The 2" width was chosen empirically to work well with this thickness to prevent shifting in the long dimension while still maintaining a reasonably flat profile. The 6" length could be shorter or longer as needed for the warming application under consideration. The optimal geometry to minimize shifting would be a cylinder because it has the smallest surface area for a given volume. Assuming that the ingredients in the warming pack are essentially incompressible, material in a fully filled cylinder fully would not be capable of shifting. As the geometry deviates farther from a cylinder, i.e. as the width increases while the thickness remains the same, the resulting cross section becomes less capable of preventing material shifting.

The temperature at each point on the surface of the warming pack is determined by the balance of the heat generation and distribution inside the warming pack and the external heat load imposed at that point. For this application, assuming uniform material distribution and negligible internal heat redistribution in the warming pack, volumetric heat generation can be assumed to be constant. However, the surface to volume ratio at the edge of the warming pack is larger and therefore the heat losses from the edges of the warming pack are larger than those from the center. Minimizing the differences caused by this effect minimizes temperature nonuniformity. The preferred embodiment of 2"×6" places all points within 1" of an edge, minimizing the differences in applied heat load and resulting in a fairly uniform surface temperature. An alternative approach to achieve a similar result would be to have a very large warming pack where most of the surface area is far from an edge, with the ideal geometry being an infinite warming pack with no edge effects.

Alternative Temperatures (Varying the Buffer Material)

For a given set of operating conditions (ambient temperature and external heat transfer coefficients) designs with different amounts of active ingredients and oxygen permeability can achieve different desired steady state operating temperatures of the warming pack. The preferred embodiment in which a thermal buffer material embodied as a phase change material chosen to limit the maximum achievable temperature of the warming pack to 42° C. can be varied to provide different maximum temperature limits. The preferred thermal buffer material is a paraffin wax, or alkane hydrocarbon, with a typical melt point of 42° C. At this melt point the material is capable of latently buffering large amounts of excess energy and limiting any further temperature rise of the chemical warming pack to 42° C. The melt point of an alkane hydrocarbon is related to its carbon chain length, and choosing different chain length hydrocarbons or mixes of those hydrocarbons as detailed in the included papers by Himran and Suwono and by Sparrow et. al. would allow for different buffering temperatures to be chosen. Different maximum achievable temperatures may be desirable based on the therapeutic goals of the warming therapy. They may, for example, yield the range of maximum temperatures in the following table.

| n-Alkanes | Number of Carbon Atoms | Melting Point ° C. |
| --- | --- | --- |
| Heptadecane | 17 | 21.9° C. |
| Octadecane | 18 | 28.1° C. |
| Nonadecane | 19 | 32.0° C. |
| Eicosane | 20 | 36.6° C. |
| Heneicosane | 21 | 40.2° C. |
| Docosane | 22 | 44.0° C. |
| Tricosane | 23 | 47.5° C. |
| Tetracosane | 24 | 50.6° C. |
| Pentacosane | 25 | 53.5° C. |
| Hexacosane | 26 | 56.3° C. |
| Heptacosane | 27 | 58.8° C. |
| Octcosane | 28 | 61.2° C. |

Burn Duration (Buffering Capacity vs. Energy Generation Capacity)

The average duration of energy generation of existing chemical warming packs employing the oxidation-reduction of iron is in the range of 4 to 12 hours. The purpose of these packs is to provide warmth during outdoor recreational activities or to provide therapeutic heat to intact skin in relatively healthy individuals. The preferred embodiment may be used, for example, to apply heat to the compromised skin of patients who may be more susceptible to thermal injury because of physiological or psychological debilitation. The risk of thermal injury can be lessened by limiting the time that the skin is exposed to elevated temperatures. The short duration of the warming pack is designed to fall within accepted time versus temperature safety curves (Stoll and Green, Henriques and Moritz).

The preferred embodiment also requires a shorter duration of energy generation for an acceptable volume of buffering component to be effective in limiting the maximum achievable temperature. A given mass of phase change material is only capable of latently buffering a certain amount of excess energy. The longer the duration of energy generation, the greater the mass of phase change material needed to buffer any excess energy. In the preferred embodiment, 10 grams of phase change material are needed to adequately buffer a 60–120 minute period of energy generation. Increasing the amount of active ingredients without changing the oxygen permeability of the warming pack would result in a longer period of heat generation, but could 'burn through' the latent heat capacity of the phase change material. When all of the material has changed phase (i.e. the latent energy storage capacity is exhausted), the temperature of the warming pack would again begin to rise. Adding additional phase change material adds to the volume of the warming pack quickly in relation to the relatively dense active ingredients, resulting in an unwieldy product unsuited for the application.

We claim:

1. A warming device, comprising:
a pack having a first side impermeable to particulate matter and to air and a second side permeable to air;
a first chamber in the pack adjacent the first side;
a second chamber in the pack adjacent the second side and in contact with the first chamber;
a flexible matrix disposed in the first chamber;
a flexible matrix disposed in the second chamber;
a first particulate material disposed in the flexible matrix of the first chamber, the first particulate material for undergoing an exothermic reaction; and,
a second particulate material disposed in the flexible matrix of the second chamber, the second particulate material for buffering the exothermic reaction.

2. The warming device of claim 1, the first particulate material including a mixture of iron, carbon, salt, and water.

3. The warming device of claim 1, the second particulate material including a phase change material.

4. The warming device of claim 1, the first flexible matrix and the second flexible matrix including a batting material.

5. The warming device of claim 1, the first flexible matrix and the second flexible matrix including a fibrillated material.

6. The warming device of claim 1, the first side being a sheet of plastic material.

7. The warming device of claim 6, the second side including a sheet of particulate-impermeable, air-permeable material, a sheet of impermeable material, and a plurality of apertures in the sheet of impermeable material.

8. The warming device of claim 1, further including one or more adhesive members on the first side.

9. The warming device of claim 1, further including an impermeable container, the pack being received in the impermeable container.

10. The warming device of claim 1, the first particulate material including a mixture of iron, carbon, salt, and water, and the second particulate material including a phase change material.

11. The warming device of claim 10, the first flexible matrix and the second flexible matrix including a fibrillated material.

12. The warming device of claim 11, the first side being a sheet of plastic material.

13. The warming device of claim 12, the second side including a sheet of particulate-impermeable, air-permeable material, a sheet of impermeable material, and a plurality of apertures in the sheet of impermeable material.

14. The warming device of claim 13, further including one or more adhesive members on the first side.

15. The warming device of claim 14, further including an impermeable container, the pack being received in the container.

16. The warming device of claim 1, wherein the second particulate material is for limiting the exothermic reaction to a maximum temperature between 29.1° C. and 61.2° C.

17. A warming device, comprising:
   a pack having a first side impermeable to particulate material and to air and a second side permeable to air;
   a first chamber in the pack adjacent the first side;
   a second chamber in the pack adjacent the second side and in contact with the first chamber;
   a flexible matrix disposed in the first chamber;
   a flexible matrix disposed in the second chamber;
   a first particulate material disposed in the flexible matrix of the second chamber, the first particulate material for undergoing an exothermic reaction; and,
   a second particulate material disposed in the flexible matrix of the first chamber, the second particulate material for buffering the exothermic reaction.

18. The warming device of claim 17, the first particulate material including a mixture of iron, carbon, salt, and water.

19. The warming device of claim 17, the second particulate material including a phase change material.

20. The warming device of claim 17, the first flexible matrix and the second flexible matrix including a batting material.

21. The warming device of claim 17, the first flexible matrix and the second flexible matrix including a fibrillated material.

22. The warming device of claim 17, the first side being a sheet of plastic material.

23. The warming device of claim 22, the second side including a sheet of particulate-impermeable, air-permeable material, a sheet of impermeable material, and a plurality of apertures in the sheet of impermeable material.

24. The warming device of claim 17, further including one or more adhesive members on the first side.

25. The warming device of claim 17, further including an impermeable container, the pack being received in the impermeable container.

26. The warming device of claim 17, the first particulate material including a mixture of iron, carbon, salt, and water, and the second particulate material including a phase change material.

27. The warming device of claim 26, the first flexible matrix and the second flexible matrix including a fibrillated material.

28. The warming device of claim 27, the first side being a sheet of plastic material.

29. The warming device of claim 28, the second side including a sheet of particulate-impermeable, air-permeable material, a sheet of impermeable material, and a plurality of apertures in the sheet of impermeable material.

30. The warming device of claim 29, further including one or more adhesive members on the first side.

31. The warming device of claim 30, further including an impermeable container, the pack being received in the container.

32. The warming device of claim 17, wherein the second particulate material is for limiting the exothermic reaction to a maximum temperature between 29.1° C. and 61.2° C.

* * * * *